United States Patent [19]

Wong et al.

[11] Patent Number: 4,983,638

[45] Date of Patent: Jan. 8, 1991

[54] CATALYST AND METHOD FOR PRODUCING LOWER ALIPHATIC ALCOHOLS

[75] Inventors: Suk-Fun Wong, Stormville, N.Y.; David A. Storm, Montvale, N.J.; Mahendra S. Patel, Hopewell Junction, N.Y.

[73] Assignee: Texaco Inc., White Plains, N.Y.

[21] Appl. No.: 380,240

[22] Filed: Jul. 17, 1989

[51] Int. Cl.$^5$ .............................................. C07C 27/06
[52] U.S. Cl. .................................................... 518/714
[58] Field of Search ............................................ 518/714

[56] References Cited

U.S. PATENT DOCUMENTS

| | | | |
|---|---|---|---|
| 4,616,040 | 10/1986 | Grazioso et al. | 518/713 |
| 4,670,473 | 6/1987 | Walker et al. | 518/714 |
| 4,831,060 | 5/1989 | Stevens et al. | 518/714 |

*Primary Examiner*—Howard T. Mars
*Attorney, Agent, or Firm*—Robert A. Kulason; James J. O'Loughlin; Dominick G. Vicari

[57] ABSTRACT

A catalyst and method for preparing a mixture of lower aliphatic alcohols is provided. The method includes reacting a mixture of carbon monoxide and hydrogen under suitable conditions of temperature and pressure in the presence of a catalyst composition. The catalyst composition comprises rhodium, cobalt, molybdenum and cesium.

17 Claims, 1 Drawing Sheet

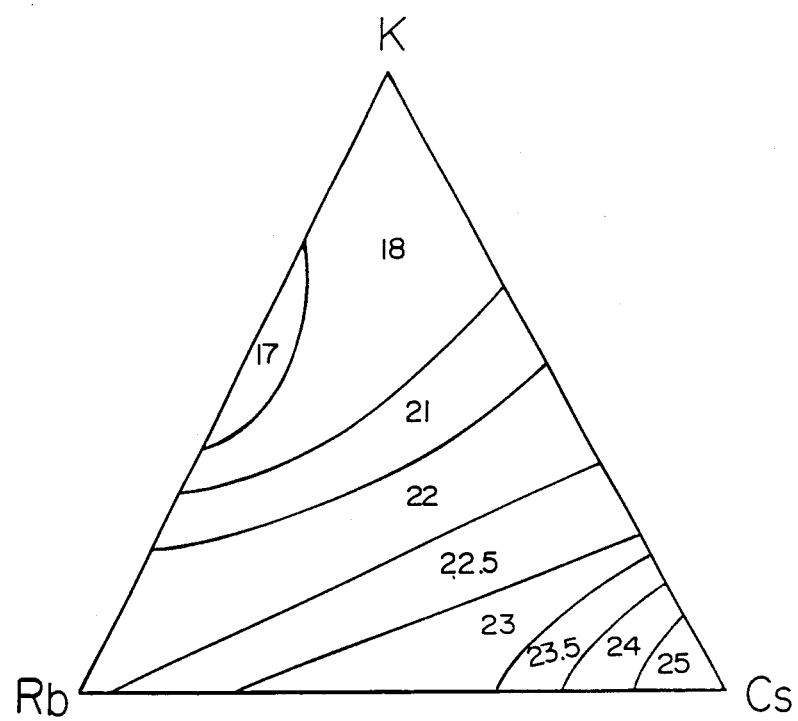

CATALYST AND METHOD FOR PRODUCING LOWER ALIPHATIC ALCOHOLS

BACKGROUND OF THE INVENTION

1. Field of the Invention

This invention relates to a catalyst and method for preparing lower aliphatic alcohols. More particularly, this invention relates to the production of a mixture of lower aliphatic alcohols characterized by containing a substantial proportion of alcohols having from 2 to 6 carbon atoms.

2. Description of Background Art

Lower aliphatic alcohols have been proposed as fuel extenders or as replacements for gasoline for fueling internal combustion engines. Certain mixtures of lower aliphatic alcohols have the EPA approval for use and are currently being marketed in the United States. The lower aliphatic alcohols can be produced from domestically available non-petroleum sources. Therefore, their use in fuels would serve to lessen the dependence of the nation on imported petroleum and petroleum products.

Hydrogen and carbon monoxide, or a synthesis gas mixture of hydrogen and carbon monoxide, can be reacted to form lower aliphatic alcohols The synthesis gas feed stream can be produced from non-petroleum sources, such as coal, biomass or other hydrocarbonaceous materials. The synthesis gas mixture itself is produced in a partial oxidation reaction of the hydrocarbonaceous material in commercially available processes, such as coal gasification.

Numerous catalysts and catalytic methods have been studied in attempts to provide a viable method for the production of aliphatic alcohols from synthesis gas or from a mixture of hydrogen and carbon monoxide. Heretofore, the emphasis has been primarily directed to the production of methanol. In contrast, the present invention is directed to a method for producing an alcohol mixture containing a substantial amount of aliphatic alcohols having 2 or more (preferably between 2 to 6) carbon atoms.

One of the shortcomings associated with the known methods of making substantial amounts of alcohols having two or more carbon atoms from synthesis gas is the substantial amount of hydrocarbons that are coproduced. Thus, where the objective is to provide higher yields of $C_2$–$C_6$ alcohols, the hydrocarbons so produced represent a major loss in carbon utilization. Surprisingly, under selected reaction conditions, the catalyst and method of the present invention result in the production of a significant fraction of aliphatic alcohols having from 2 to 6 carbon atoms, without the substantial coproduction of undesirable hydrocarbons.

U.S. Pat. No. 4,096,164 discloses a process for reacting hydrogen and carbon monoxide in the presence of a solid catalyst comprising rhodium with molybdenum or tungsten to produce two carbon atom oxygenated hydrocarbons in which ethanol is the major component. This disclosure is incorporated herein by reference.

U.S. Pat. No. 4,380,589 discloses a Fischer-Tropsch process for producing hydrocarbons with improved selectivity to $C_2$–$C_4$ olefins by contacting hydrogen and carbon monoxide in the presence of a catalyst. The catalyst disclosed comprises molybdenum, a promoter comprising an alkali or alkaline earth metal and a binder comprising an iron-containing calcium aluminate cement.

U.S. Pat. No. 4,607,055 discloses a process for producing lower aliphatic alcohols from a mixture of carbon monoxide and hydrogen in the presence of a catalyst comprising molydbdenum; a metal from the group consisting of cobalt, iron and nickel; and silver. The catalyst is modified by the addition of a promoter from the class consisting of potassium, cesium and rubidium. This disclosure is incorporated herein by reference.

U.S Pat. No. 4,661,525 discloses a process for producing lower aliphatic alcohols from a mixture of carbon monoxide and hydrogen in the presence of a catalyst comprising molybdenum and a metal selected from the group consisting of cobalt, iron and nickel which has been promoted by an alkali metal selected from the group consisting of potassium, cesium and rubidium. This disclosure is incorporated herein by reference.

EPA No. 119609 discloses a process for producing alcohols from synthesis gas using a catalyst containing molybdenum with tungsten, rhenium and an alkali metal. This disclosure is incorporated herein by reference. E.P. No. 79132 discloses a similar process in which the catalyst contains rhenium, molybdenum and potassium.

Co-assigned application Ser. No. 939,392 filed on Dec. 12, 1986 is directed to a process for producing lower aliphatic alcohols from a mixture of carbon monoxide and hydrogen in the presence of a catalyst comprising rhodium, molybdenum and an alkali metal. This disclosure is incorporated herein by reference.

Previous catalytic methods have been notably effective for converting carbon monoxide and hydrogen feedstocks into hydrocarbons or methanol, but none have been particularly effective for providing a substantial yield of a lower aliphatic alcohol mixture at a moderate reaction temperature and reaction pressure

SUMMARY OF THE INVENTION

It has now been discovered that a mixture of carbon monoxide and hydrogen can be reacted to form a mixture of lower aliphatic alcohols containing a substantial amount of lower aliphatic alcohols having from 2 to 6 carbon atoms. This reaction is conducted by contacting a feed mixture containing carbon monoxide and hydrogen, such as synthesis gas, with a novel catalyst composition which produces high yields of lower aliphatic alcohols under suitable conditions of temperature and pressure. The catalyst composition comprises a mixture of rhodium, cobalt, molybdenum and cesium. Surprisingly, the prescribed catalyst produces high yields of the desired alcohols, i.e., those other than methanol, at a relatively low reaction temperature and pressure.

The lower aliphatic alcohols produced in accordance with the method of the present invention are useful as, among other things, a blending component in hydrocarbon motor fuels.

BRIEF DESCRIPTION OF THE DRAWING

FIG. 1 is a contour plot illustrating the percent of higher alcohols (as opposed to methanol) produced among various mixtures of certain alkali metals.

DETAILED EMBODIMENTS OF THE INVENTION

In accordance with this invention, a mixture of carbon monoxide and hydrogen as, for example, a synthesis gas mixture of same, is reacted in the presence of a catalyst composition comprising rhodium, cobalt and molybdenum which has been modified by the addition of a cesium promoter As indicated in FIG. 1, when cesium is employed as the promoter, the catalyst composition produces the greatest percentage of higher alcohols, i.e., 25 percent.

The catalyst composition can be prepared in a number of ways known in the art. In general, the use of a catalyst support or carrier comprising a relatively refractory, porous, adsorptive and high surface area material is preferred. Conventional carriers or supports, such as alumina, silica, titania, magnesia, silica-alumina and boron phosphates, are suitable support materials for preparing the catalyst of the present invention. Other conventional carriers or supports are to be considered within the scope of this invention. The disclosure in U.S. Pat. No. 4,098,683 is illustrative and is incorporated herein by reference.

A preferred method for preparing the catalyst composition is to impregnate the carrier with the metal components in the form of a soluble salt. The metal components may be impregnated simultaneously or sequentially. The impregnated carrier is dried and then calcined according to known procedures.

The catalyst composition comprises from about 0.1 to about 3 weight percent rhodium, from about 0.1 to about 3 weight percent of cobalt, from about to about 12 weight percent molybdenum and from about 1 to about 20 weight percent of cesium. Preferably, all of the components are well dispersed on a carrier or support, the most preferred being gamma-alumina. A preferred catalyst composition comprises from about 0.5 to about 1.5 weight percent rhodium, from about 0.5 to about 1.5 weight percent cobalt, from about 3 to about 12 weight percent molybdenum and from about 2 to about 10 weight percent cesium.

In another embodiment, the catalyst composition of the present invention further includes from about 1 part per million to about 100 parts per million of chlorine, which, surprisingly, promotes the production of $C_2$-$C_6$ alcohols relative to the production of hydrocarbons, thereby improving the carbon efficiency of the present method.

The carbon monoxide and hydrogen, or a mixture of same, employed to form the lower aliphatic alcohols in this method can be provided from any available source. One particularly useful source is synthesis gas which, for instance, is produced in the gasification of hydrocarbonaceous materials, such as oil, coals and biomass. An effective gasification process is described in U.S. Pat. No. 3,544,291 where a hydrocarbonaceous fuel is partially oxidized with a free oxygen-containing gas in a gas generator. In general, the mole ratio of hydrogen to carbon monoxide employed in this process should range from about 0.5 to about 5 moles of hydrogen per mole of carbon monoxide, with the preferred ratio being from about 0.5 to about 2 moles of hydrogen per mole of carbon monoxide.

The reaction conditions for effecting the conversion of the carbon monoxide-hydrogen feed into lower aliphatic alcohols employing the catalyst of the present invention include a reaction temperature ranging from about 240° C. to about 400° C. with the preferred temperature ranging from about 260° C. to about 310° C.

Effective hydrogenation of carbon monoxide is accomplished at elevated pressures. An effective pressure range for this process is from about 500 to about 3500 psig. A preferred pressure range is from about 750 to about 1500 psig.

The space velocity employed to effect the conversion of carbon monoxide and hydrogen over the prescribed catalyst to produce the aliphatic alcohols is a significant feature of this method. In general, the space velocity, that is the volume of gas passed through a given volume of catalyst per hour expressed as GHSV ($hr^{-1}$), must be at least about 1000. A preferred range is from about 5000 to about 20,000. A highly effective method is realized when the space velocity employed ranges from about 5,000 to about 15,000.

The present invention is more fully described in Examples I-XXII. In each example, approximately 30 cc of catalyst was diluted with 10 cc of alpha-alumina and packed into a $\frac{1}{4}$" I.D. type 316 stainless steel reactor tube. The catalyst was first reduced in flowing hydrogen for 4 hours at 400° C., 1500 psig and 10,000 $hr^{-1}$ GHSV. The catalyst was then cooled to reaction temperature and subjected to a mixture of hydrogen and carbon monoxide in the ratio of 2:1. Reaction pressure was 1500 psig and the GHSV was 10,000 $hr^{-1}$. The gases emerging from the exit of the reactor were sent through a condenser which liquefied the alcohol and water products. The resulting liquids and non-condensable gases were analyzed by gas chromatography.

Catalytic performance of the catalyst compositions produced in accordance with Examples I-XIV was evaluated in accordance with the following definitions:

1. Selectivity to Alcohols (S):

$$S = \frac{\text{Moles of Carbon in alcohols product}}{\text{Moles of Carbon in alcohol and hydrocarbon}} \times 100$$

2. Productivity for Alcohols (P):

$$P = \frac{\text{Weight of Alcohols produced per hour}}{\text{Weight of Catalyst}}$$

3. Percentage of Higher Alcohols in Alcohol Mixture (HA):

$$\% HA = \frac{\text{Weight of Alcohols in Product-Weight of Methanol in Product}}{\text{Weight of Alcohols in Product}} \times 100$$

4. Carbon Efficiency (CE):

$$CE = \frac{\text{Moles of Alcohols Other than Methanol in Product}}{\text{Moles of Hydrocarbons in Product}}$$

5. TR = Reaction Temperature

EXAMPLE I

A catalyst was prepared by first impregnating gamma-alumina (Norton SA637) with a 0.06 M solution of ammonium heptamolybdate (Aesai) until the point of incipient wetness. The catalyst precursor was calcined in flowing air (2 SCFH) at 500° C. for 3 hours. The precursor was then coimpregnated with cobalt nitrate (0.17 M) and rhodium nitrate (0.14 M) until the point of incipient wetness. The precursor was dried overnight at 120° C. Cesium carbonate was added to the catalyst to obtain a catalyst composition including the following components (weight percent): 3.38% Mo, 1.14% Rh, 0.7% Co, and 9.21% Cs.

EXAMPLE II

A catalyst was prepared according to Example I except that the concentration of the ammonium heptamolybdate solution was 0.14 M. The composition of the catalyst was (weight percent): 6.33% Mo, 1.06% RH, 0.66% Co and 8.99% Cs.

EXAMPLE III

A catalyst was prepared according to Example I except that the concentration of the ammonium heptamolybdate solution was 0.30 M. The composition of the catalyst was (weight percent): 12.1% Mo, 0.93% Rh, 0.68% CO and 9.87% Cs.

The results of the evaluation of the catalysts prepared in Examples I-III are shown in Table I. It is evident that the selectivity is strongly influenced by the concentration of molybdenum and that high selectivity is obtained for molybdenum concentrations in the range of about 3 to about 6%.

EXAMPLE IV

A catalyst was prepared according to Example I except that the concentration of the ammonium heptamolybdate solution was 0.14 M and that of the cobalt solution was 0.05 M. The composition of the catalyst was (weight percent) 6.20% Mo, 0.20% Co, 0.99% Rh, and 9.40% Cs.

EXAMPLE V

A catalyst was prepared according to Example I except that the concentration of the ammonium heptamolybdate solution was 0.14 M. The composition of the catalyst was (weight percent) 6.63% Mo, 0.68% Co, 1.06% Rh, and 8.99% Cs.

EXAMPLE VI

A catalyst was prepared according to Example V except that the concentration of the cobalt nitrate was 0.29 M. The composition of the catalyst was (weight percent): 6.30% Mo, 1.10% Co, 1.10% Rh, and 8.76% Cs.

The catalysts prepared and described in Examples IV-VI were evaluated as described above. The results are shown in Table II, where it is evident that more higher alcohols are made with catalyst containing more cobalt.

The catalysts described in Examples I, III and V were evaluated at two different temperatures. The results are shown in Table III, where it is evident that more higher alcohols are made for temperature above 280° C.

The catalyst described in Example I was evaluated at two different ratios of hydrogen to carbon monoxide. The results are shown in Table IV, where it is evident that more higher alcohols are made with synthesis gas with a hydrogen/carbon monoxide molar ratio less than one.

EXAMPLES VII-XVI

A catalyst precursor containing molybdenum, rhodium and cobalt was prepared according to Example I. The precursor was divided into ten equal amounts and each was impregnated with potassium carbonate, rubidium carbonate and/or cesium carbonate according to the schedule shown in Table V. In these catalysts the number of moles of alkali atoms was about 0.08 moles of atoms per 100 g of catalyst. These catalysts were evaluated as described above. The results are shown in Table V and FIG. 1 where it is evident that more higher alcohols are made when the alkali metal is cesium.

TABLE I (Effect of Mo)

| Example | Mo (weight Percent) | Tr | S | P | % HA |
|---|---|---|---|---|---|
| I | 3.4 | 282 | 82 | 0.4 | 21 |
| II | 6.3 | 286 | 75 | 0.4 | 28 |
| III | 12.1 | 288 | 58 | 0.2 | 45 |

TABLE II (Effect of Co)

| Example | Co (Weight percent) | Tr | S | P | % HA |
|---|---|---|---|---|---|
| IV | 0.2 | 284 | 75 | 0.3 | 29 |
| V | 0.7 | 284 | 73 | 0.3 | 31 |
| VI | 1.1 | 283 | 74 | 0.3 | 33 |

TABLE III (Effect of Temp.)

| Example | Mo (Weight Percent) | Tr | S | P | % HA |
|---|---|---|---|---|---|
| I | 3.4 | 284 | 81 | 0.4 | 22 |
|  |  | 304 | 70 | 0.7 | 29 |
| V | 6.3 | 282 | 72 | 0.3 | 34 |
|  |  | 306 | 60 | 0.4 | 41 |
| III | 12.0 | 288 | 56 | 0.2 | 46 |
|  |  | 312 | 52 | 0.3 | 48 |

TABLE IV (Effect of CO/H$_2$)

| Example | H$_2$/CO | Tr | S | P | % HA |
|---|---|---|---|---|---|
| I | 2/1 | 284 | 81 | 0.4 | 22 |
| I | (0.7–0.9)/1 | 289 | 78 | 0.2 | 34 |

TABLE V (Effect of Alkali)

| Example | K | Rb | Cs | Tr | S | P | % HA |
|---|---|---|---|---|---|---|---|
| V | 1 | 0 | 0 | 290 | 85 | 0.6 | 18 |
| VI | 0 | 1 | 0 | 290 | 81 | 0.5 | 22 |
| VII | 0 | 0 | 1 | 290 | 78 | 0.4 | 25 |
| VIII | ½ | ½ | 0 | 290 | 88 | 0.5 | 17 |
| IX | ½ | 0 | ½ | 290 | 85 | 0.4 | 19 |
| X | 0 | ½ | ½ | 290 | 81 | 0.4 | 23 |
| XI | ⅓ | ⅓ | ⅓ | 290 | 83 | 0.4 | 22 |
| XII | ⅔ | 1/6 | 1/6 | 290 | 87 | 0.4 | 18 |
| XIII | 1/6 | ⅔ | 1/6 | 290 | 84 | 0.3 | 22 |
| XIV | 1/6 | 1/6 | ⅔ | 290 | 77 | 0.4 | 24 |

EXAMPLE XVII

A catalyst was prepared by first impregnating gamma-alumina (Norton SA637) with a 0.06 M solution of ammonium heptamolybdate (Aesai) until the point of incipient wetness to provide a catalyst precursor. The catalyst precursor was calcined in flowing air (2 SCFH) at 500° C. for 3 hours. The precursor was then impregnated with a 0.14 M solution of rhodium nitrate until the point of incipient wetness. The precursor was dried overnight at 120° C. The precursor was then impregnated with a 0.5 M solution of cesium carbonate. The composition of the catalyst was (weight percent) 2.67% Mo, 1.1% Rh, 9.3% Cs.

EXAMPLES XVIII-XXII

Five catalysts were prepared according to Example XVII except that small amounts of a 0.1 N solution of hydrochloric acid was added to the 0.14 M solution of rhodium nitrate. The chlorine concentration employed in the catalysts of Examples XVII-XXII is provided in Table VI.

The catalysts of Examples XVII-XXII were evaluated for carbon efficiency. The reaction temperatures and results of the evaluation are also provided in Table VI.

TABLE VI

| Example | Cl | Tr | CE |
|---------|------|-----|------|
| XVII    | —    | 290 | 1.10 |
| XVIII   | 1 ppm | 283 | 1.35 |
| XIX     | 10 ppm | 286 | 1.42 |
| XX      | 20 ppm | 284 | 1.50 |
| XXI     | 100 ppm | 285 | 1.48 |
| XXII    | 1900 ppm | 284 | 1.08 |

As these data demonstrate, when small amounts of chlorine are added to the catalyst composition of the present invention, the production of $C_2$-$C_6$ alcohols is promoted relative to the production of hydrocarbons, thereby increasing the carbon efficiency of the present process.

What is claimed is:

1. A method for preparing lower aliphatic alcohols which comprises reacting carbon monoxide and hydrogen in the presence of a catalyst composition which includes rhodium, cobalt, molybdenum, cesium and from about 1 part per million to about 100 parts per million of chlorine.

2. The method of claim 1 wherein said catalyst composition further includes a support for supporting said rhodium, cobalt, molybdenum and cesium.

3. The method of claim 2 wherein said support is selected from the group consisting of alumina, silica, titania, magnesia, silica-alumina and boron phosphates.

4. The method of claim 3 wherein said support is gamma-alumina.

5. The method of claim 1 wherein said reaction takes place at a temperature of about 240° C. to about 400° C.

6. The method of claim 5 wherein said reaction takes place at a temperature of about 260° C. to about 310° C.

7. The method of claim 1 wherein said reaction takes place at a pressure of about 500 to about 3500 psig.

8. The method of claim 7 wherein said reaction takes place at a pressure of about 750 to about 1500 psig.

9. The method of claim 1 wherein said reaction takes place at a gas hourly space velocity of at least about 1000 hr$^{-1}$.

10. The method of claim 9 wherein said reaction takes place at a gas hourly space velocity of between about 5000 hr$^{-1}$ to about 20,000 hr$^{-1}$.

11. The method of claim 1 wherein said catalyst composition includes from about 0.1 to about 3 weight percent of rhodium; from about 0.1 to about 3 weight percent of cobalt; from about 1 to about 12 weight percent of molybdenum; and from about 1 to about 20 weight percent of cesium.

12. The method of claim 11 wherein said catalyst composition includes from about 0.5 to about 1.5 weight percent of rhodium; from about 0.5 to about 1.5 weight percent of cobalt; from about 3 to about 12 weight percent of molybdenum; and from about 2 to about 10 weight percent of cesium 13. The method of claim 12 wherein the total number of moles of cesium is from about 0.02 to about 0.09 per 100 g of catalyst.

14. The method of claim 1 wherein said catalyst composition further comprises from about 1 part per million to about 100 parts per million of chlorine.

15. The method of claim 1 wherein the source of said carbon monoxide and hydrogen is synthesis gas.

16. The method of claim 1 wherein the mole ratio of hydrogen to carbon monoxide is from about 0.5 to about 5 moles of hydrogen per mole of carbon monoxide.

17. A method for preparing lower aliphatic alcohols which comprises reacting carbon monoxide and hydrogen in the presence of a catalyst composition at a temperature of about 240° C. to about 400° C., at a pressure of about 500 to about 3500 psig. and at a gas hourly space velocity of at least about 1000 hr$^{-1}$, said catalyst composition including from about 0.5 to about 1.5 weight percent of rhodium, from about 0.5 to about 1.5 weight percent of cobalt, from about 3 to about 12 weight percent of molybdenum, from about 2 to about 10 weight percent of cesium, wherein the total number of moles of cesium is from about 0.02 to about 0.09 per 100 grams of catalyst, and from about 1 part per million to about 100 parts per million of chlorine.

* * * * *